United States Patent [19]

Blake, III et al.

[11] Patent Number: 5,171,300

[45] Date of Patent: * Dec. 15, 1992

[54] DISPOSABLE HYPODERMIC SYRINGE

[75] Inventors: Joseph W. Blake, III, New Canaan; Thomas E. Sloane, Jr., West Redding, both of Conn.

[73] Assignee: Medtech Group, Inc., South Plainfield, N.J.

[*] Notice: The portion of the term of this patent subsequent to Jan. 22, 2008 has been disclaimed.

[21] Appl. No.: 869,862

[22] Filed: Apr. 16, 1992

Related U.S. Application Data

[63] Continuation of Ser. No. 627,235, Dec. 14, 1990, abandoned, which is a continuation-in-part of Ser. No. 296,495, Jan. 12, 1989, Pat. No. 4,986,813, which is a continuation-in-part of Ser. No. 150,621, Feb. 8, 1988, abandoned.

[51] Int. Cl.$^5$ ............................................. A61M 5/00
[52] U.S. Cl. ..................................... 604/110; 604/195; 604/220
[58] Field of Search ........ 604/110, 263, 192, 195–198, 604/240, 218, 220; 128/919

[56] References Cited

U.S. PATENT DOCUMENTS

| 4,675,005 | 6/1987 | Deluccia | 604/110 |
|---|---|---|---|
| 4,692,156 | 9/1987 | Haller | 604/195 |
| 4,747,830 | 5/1988 | Gloyer et al. | 604/110 |
| 4,770,655 | 9/1988 | Haber et al. | 604/110 |
| 4,790,822 | 12/1988 | Haining | 604/110 |
| 4,898,589 | 2/1990 | Dolgin | 604/198 |
| 4,909,794 | 3/1990 | Haber et al. | 604/195 |
| 4,932,939 | 6/1990 | Magre et al. | 604/110 |
| 4,944,723 | 7/1990 | Haber et al. | 604/110 |
| 4,978,340 | 12/1990 | Terrill et al. | 604/195 |
| 4,986,813 | 1/1991 | Blake et al. | 604/110 |
| 5,030,208 | 7/1991 | Novacek et al. | 604/195 |
| 5,066,281 | 11/1991 | Stevenson-Michener | 604/110 |

Primary Examiner—C. Fred Rosenbaum
Assistant Examiner—Mark O. Polutta
Attorney, Agent, or Firm—Arthur L. Plevy

[57] ABSTRACT

A syringe and needle assembly having a piston that is formed to engage and retract the needle assembly into the syringe barrel. The piston includes a spring member that is elastically deformed by the attachment of the piston to the needle assembly. The spring member causes the needle assembly to be spring biased into a canted position so that, once retracted into the syringe barrel, the needle assembly cants to an inoperable position.

16 Claims, 4 Drawing Sheets

DISPOSABLE HYPODERMIC SYRINGE

This application is a continuation of Ser. No. 07/627,235 filed Dec. 14, 1990 ABN which is a continuation-in-part of Ser. No. 07/296,495 filed Jan. 12, , now U.S. Pat. No. 4,986,813, issued Jan. 22, 1991 and entitled DISPOSABLE HYPODERMIC SYRINGE which was a continuation-in-part of U.S. patent application Ser, No. 07/150,621 filed Feb. 8, 1988 and now abandoned.

BACKGROUND OF THE INVENTION

This invention relates to hypodermic syringe and needle combinations. More particularly, it relates to a hypodermic syringe and needle combination wherein the needle can be permanently retracted into the syringe barrel.

Health care workers, such as nurses, and even housekeeping personnel are becoming more fearful of exposure to infectious diseases, such as hepatitis, AIDS, and the like through transmission by the accidental impalation with used hypodermic needles.

It has, therefore, become desirable to provide syringe and needle combinations which will reduce the possibility of such accidents.

Used needle and syringe combinations have also been implicated in drug abuse situations.

It is, therefore, also desirable to provide such combinations which may not easily be reused for such purposes.

Disposable hypodermic needle and syringe combinations, however, must be inexpensive to produce and easy to operate if they are to be widely utilized.

U.S. Pat. No. 4,592,744 describes such a combination wherein:

a standard syringe and needle are mounted in a clear plastic sheath. The needle extends through a hole in the bottom of the sheath. The end of the needle is covered with a cap. To use, the cap is removed and the standard medical procedures are carried out in the usual way but with the syringe still inside of the clear plastic sheath. After use, the syringe and needle are drawn back into the sheath and the needle is completely within the confines of the plastic sheath. Flanges within the sheath catch behind the lip of the needle as the syringe is withdrawn, trapping the needle within the sheath. The needle is thus unable to protrude at either end. (Column 2 lines 16 to 28)

The above system suffers from the fact that it requires a separate sheath to contain the used needle. The cost of the combination, which can be reused is, therefore, increased by the requirement for the separate sheath.

Furthermore, if an abuser were to wish to reuse the needle and syringe it would only be necessary to cut away the sheath and re-attach the needle to the syringe.

U.S. Pat. No. 4,702,738 discloses a disposable needle and syringe combination comprising a retractable sheath to cover the needle, after use, and lock in place thereby preventing accidental pricking by the exposed needle or reuse for drug abuse.

This system also suffers from the disadvantages noted above. Thus, if an abuser were to wish to reuse the combination for drug abuse, it would only be necessary to cut through the sheath thereby exposing the needle for reuse.

U.S. Pat. No. 4,747,829 discloses a "Prefilled syringe . . ." which suffers from the fact that it can only be used in "pre-filled" condition thus limiting its value. One would be required to have a large number of syringes if one would have many compositions to dispense. Furthermore, one could not use this syringe to withdraw fluids from a source such as a patient.

In addition, the preferred embodiment depends upon a pre-stressed needle which bows out of alignment with the plunger upon withdrawal from the barrel stem. This, of course, creates difficulties in positioning the needle within the syringe.

In U.S. Pat. No. 4,747,830 there is disclosed a retractable needle syringe wherein the needle is prevented from re-extension through the barrel stem, after being withdrawn. The Patent includes cooperating latching means, in the upper portions of the barrel inner wall and the outer wall of the plunger, which lock the needle assembly in an elevated position. The latching means are complex and would require expensive tooling.

The Patent also discloses means, (see e.g., FIG. 15), in the plunger head to engage the needle assembly for removal from the barrel stem. The engagement means 134 would have to break through a wall of a resilient flexible piston 136, which would require considerable force, before it would engage the needle assembly. Furthermore, at the time it would be necessary to break through the wall, said wall would be entrapped between the engaging means of the plunger and needle assembly thereby increasing the difficulty of breaking through it.

U.S. Pat. No. 4,770,655 describes a retractable needle syringe wherein the needle is canted relative to the longitudinal axis, within the barrel, after its use has been completed. In the disclosure the pin head at the proximal end of the needle, which is press-fitted into the exit stem of the barrel, is grasped by a flexible cavity at the distal end of the plunger. The cavity has a steplike structure of differing lengths and orientation which will cause the needle engaged therewith to cant relative to the longitudinal axis of the barrel.

The above invention suffers, inter alia, from the disadvantages of having a needle which is press-fitted into the barrel stem. That can result in the needle being pushed back into the barrel when an attempt is made to insert it into a receptacle for injection withdrawal. In addition, gripping of the narrow and thin pinhead of the needle and subsequent drawing of same into the stepped cavity of the plunger head would be difficult to achieve. The complex structure of the plunger head would also increase the costs of manufacturing the syringes.

U.S Pat. No. 4,955,869 discloses a retractable needle syringe comprising spring means at the distal end of the plunger causing the needle assembly thereof to be canted relative to the longitudinal axis of the barrel when said needle assembly has been retracted thereinto. The spring means comprises a compressible wedge-shaped seal at the distal end of the plunger. The wedge-shaped seal compresses upon engagement of the needle by an engaging means when said needle assembly is engaged by the barrel stem.

Among the disadvantages, is that the compressible spring means must comprise a material different from the plunger head. As a consequence, the plunger and spring means cannot be fabricated in a single step and the cost of manufacturing the syringe is increased.

It has now been found that the disadvantages of the prior art may be avoided by use of the needle and syringe combination of the present invention.

SUMMARY OF THE INVENTION

The present invention provides a syringe and needle assembly wherein the needle can be selectively retracted into the syringe and canted out of position; thus permanently destroying the functionality of the assembly. The present invention assembly includes a syringe barrel having a needle assembly removably threaded into the neck of the barrel. A plunger is reciprocally positionable within the syringe barrel for drawing and displacing fluids into the syringe through the needle assembly. An attachment means is formed on the head of the plunger, for selectively attaching the plunger to the needle assembly, so that the plunger may retract the needle assembly into the syringe barrel. The piston also includes a spring bias means that is elastically deformed by the attachment of the piston to the needle assembly. The spring bias means, when deformed, acts to bias the needle assembly into a canted position.

The attachment means, formed on the piston, fits into a cavity, formed in the needle assembly, when the piston is fully depressed into the syringe barrel. Once the attachment means has past into the cavity, the piston can be selectively attached to the needle assembly by rotating the piston relative to the needle assembly. Once the piston and needle assembly are attached, a continued rotation of the piston will cause the needle assembly to rotate and unthread from the neck of the syringe barrel. Once the needle assembly is unthreaded, the needle assembly can be retracted into the syringe barrel by the retraction of the piston. When the needle assembly no longer contacts the neck of the syringe barrel, there exists no forces that can counteract the spring bias means formed on the plunger head. Consequently, the spring bias means returns to its original unbiased position, causing the attached needle assembly to cant within the syringe barrel. Once canted, the needle prevents the plunger from advancing in the syringe barrel, thus the syringe and barrel assembly are rendered inoperable.

BRIEF DESCRIPTION OF THE FIGURES

For a better understanding of the present invention, reference is made to the following description of an exemplary embodiment thereof, considered in conjunction with the accompanying drawings, in which.

DETAILED DESCRIPTION OF THE PREFERRED EMBODIMENT

This application is a continuation-in-part of U.S. Pat. No. 4,986,813, issued Jan. 22, 1991. The specification and drawings of U.S. Pat. No. 4,986,813 are therefore incorporated herein by reference to facilitate the description of the present invention.

Figure 1:
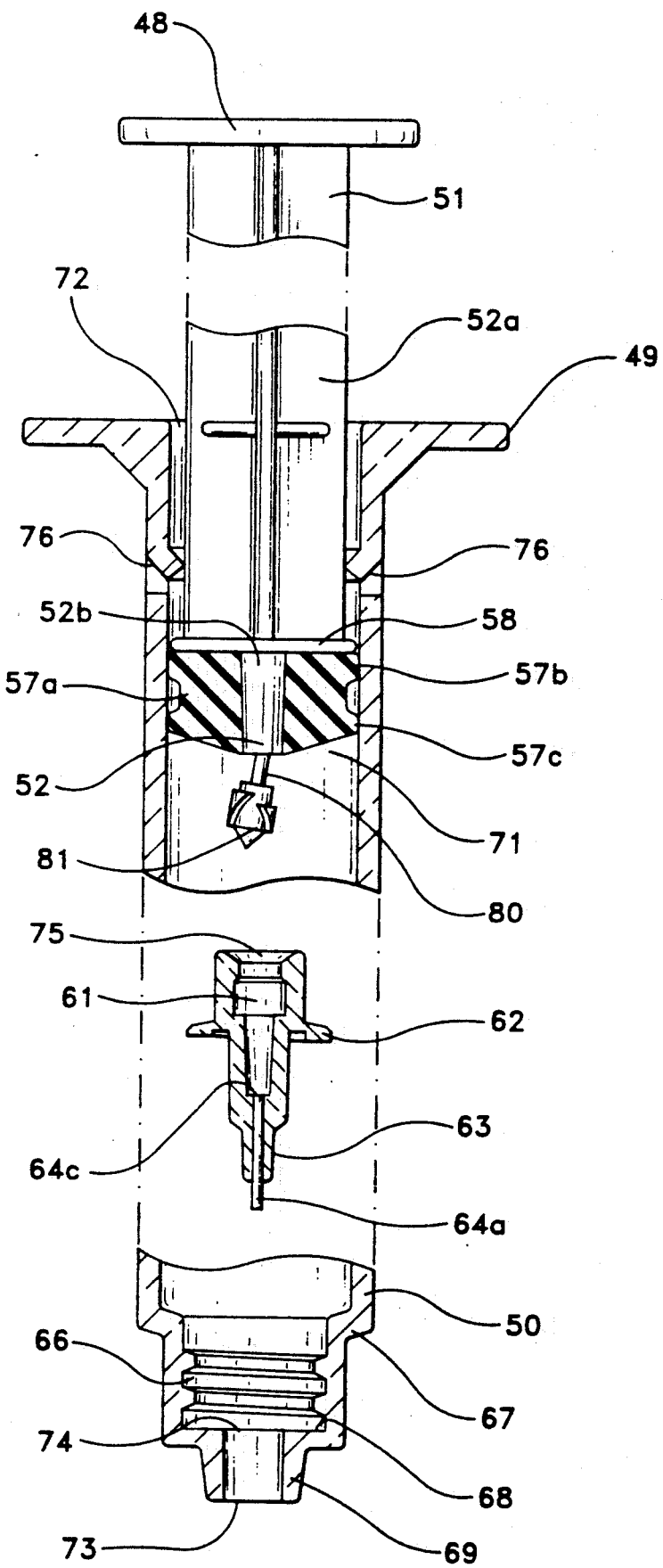
FIG. 1 is an exploded side view of one exemplary embodiment of the present invention hypodermic syringe and needle combination, the figure shown is partially sectioned to facilitate consideration and discussion.

Referring to FIG. 1, the present invention syringe and needle assembly 2 is shown comprising a cylindrical syringe barrel in which a plunger assembly and needle assembly are placed. The syringe barrel is formed from longitudinally extended wall 50 defining an elongated cavity 71. The proximate end of the syringe barrel terminates in a large opening 72. A flange 49 is formed on the exterior of the syringe barrel at the large opening 72 to facilitate the manipulation of the syringe barrel.

The distal end of the syringe barrel is formed into a neck region wherein the wall 50 of the syringe barrel tapers inwardly along an annular protrusion 67. The annular protrusion 67 leads to a threaded region wherein an annular groove 66 is formed in the walls of the syringe barrel in a threaded pattern. The bottom of the threaded region terminates in a bottom wall 68 through which a small opening 74 is centrally formed. The small opening 74 leads into a hollow stem 69, that terminates in a bottom opening 73.

Positioned in the syringe barrel is a plunger 51. The plunger 51 reciprocally moves along the longitudinal axis of the syringe barrel such as is typical of hypodermic syringes. The plunger is formed from a longitudinally elongated member 52a which acts as the plunger shaft. The top of the plunger shaft terminates in a flat gripping means 48 by which the piston 51 can be driven into the syringe barrel or rotated within the syringe barrel by manual manipulation.

A circular horizontal disc 58 is positioned on the plunger shaft opposite the gripping means 48. The circular disc 58 is wider than the general girth of the elongated member 52a forming the piston shaft. As such, the circular disc 58 abuts against a stopping projection 76 when retracted in the syringe barrel. The stopping projection 76 are extensions formed on the syringe barrel wall 50 that extend into the barrel cavity 76. The abutment of the circular disc against the stopping projection 76 prevents the piston 51 from being withdrawn from the syringe barrel cavity 76.

Protruding forward, from the side of the circular disc 58 opposite the plunger shaft, is the plunger head 52b. The plunger head 52, proximate the circular disc 58, is surrounded by a circular grommet that serves as the piston 57a. The piston 57a at its upper end 57b and lower end 57c contacts the syringe barrel creating a fluid impervious seal with the syringe barrel.

The plunger head 52b is formed to have a coupling assembly extend forward, beyond the piston 57a, in the syringe barrel. The coupling assembly includes a distal portion 81 that is formed as the connector means for engaging the needle assembly, as will later be described. The distal portion 81 is supported by the proximal portion 80 of the plunger head 52b. The proximal portion 80 is a flexible elongated member that holds the distal portion 81 of the plunger head 52b at an angle relative to the longitudinal axis of the syringe barrel.

Positioned in the distal end of the syringe barrel is the needle assembly. The needle assembly consists of a base in which is formed a cavity 61. The cavity 61 is accessed by a large tapered opening 75 that faces the plunger 51 in the syringe barrel. The cavity 61 connects to a proximal opening 64c that connects the cavity 61 to lumen of a needle, or similar hollow tube, that is supported by the base hub 63 of the needle assembly.

On the exterior of the needle assembly are formed outwardly-directed projections 62. The projections 62 fit into the annular grooves 66 formed in the neck of the syringe barrel; thus the needle assembly can be threaded into the neck of the syringe barrel. Prior to the use of the present invention, the needle assembly is threaded into the neck of the syringe barrel such that a fluid impervious seal is created between the needle assembly and the syringe barrel.

Figure 2:
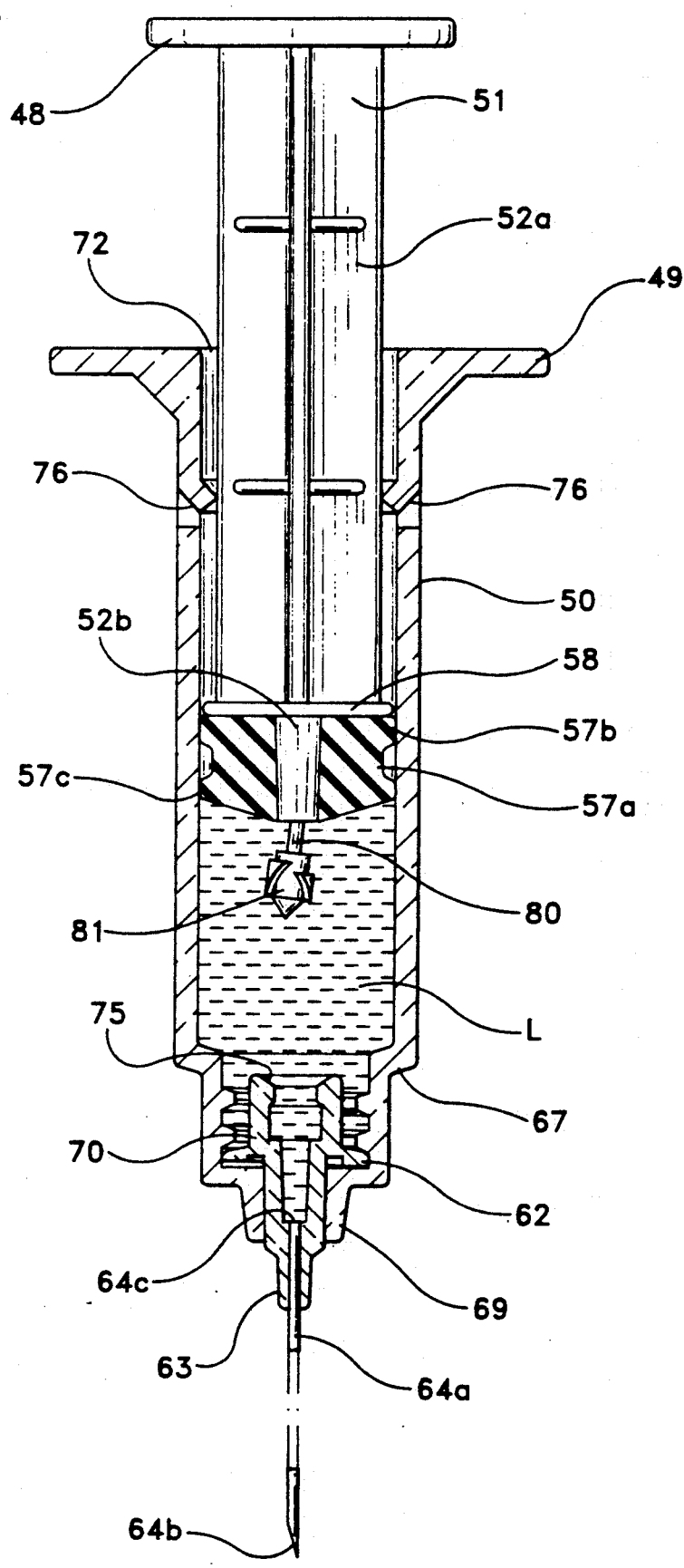
FIG. 2 is a partially sectioned side view of the embodiment shown in FIG. 1 as it would appear when filled with a desired liquid.

Referring to FIG. 2, the operation of the present invention syringe and needle assembly can begin to be described. To use the present invention syringe and needle assembly, a desired amount of liquid L is drawn into the syringe barrel, through the needle, in a manner typical and well known for hypodermic syringes, i.e. the sharp distal end 64b of the needle is inserted into a liquid source and the plunger 51 is retracted within the syringe barrel. The liquid L can then be discharged from the syringe barrel by advancing the plunger 51 and displacing the liquid L through the needle. The process of drawing and discharging liquid L to and from the syringe barrel may be repeated a many times as desired by an operator.

When the plunger 51 is fully advanced into the syringe barrel, the coupling assembly of the plunger head 52b enters into the cavity 61 of the needle assembly.

Figure 3:
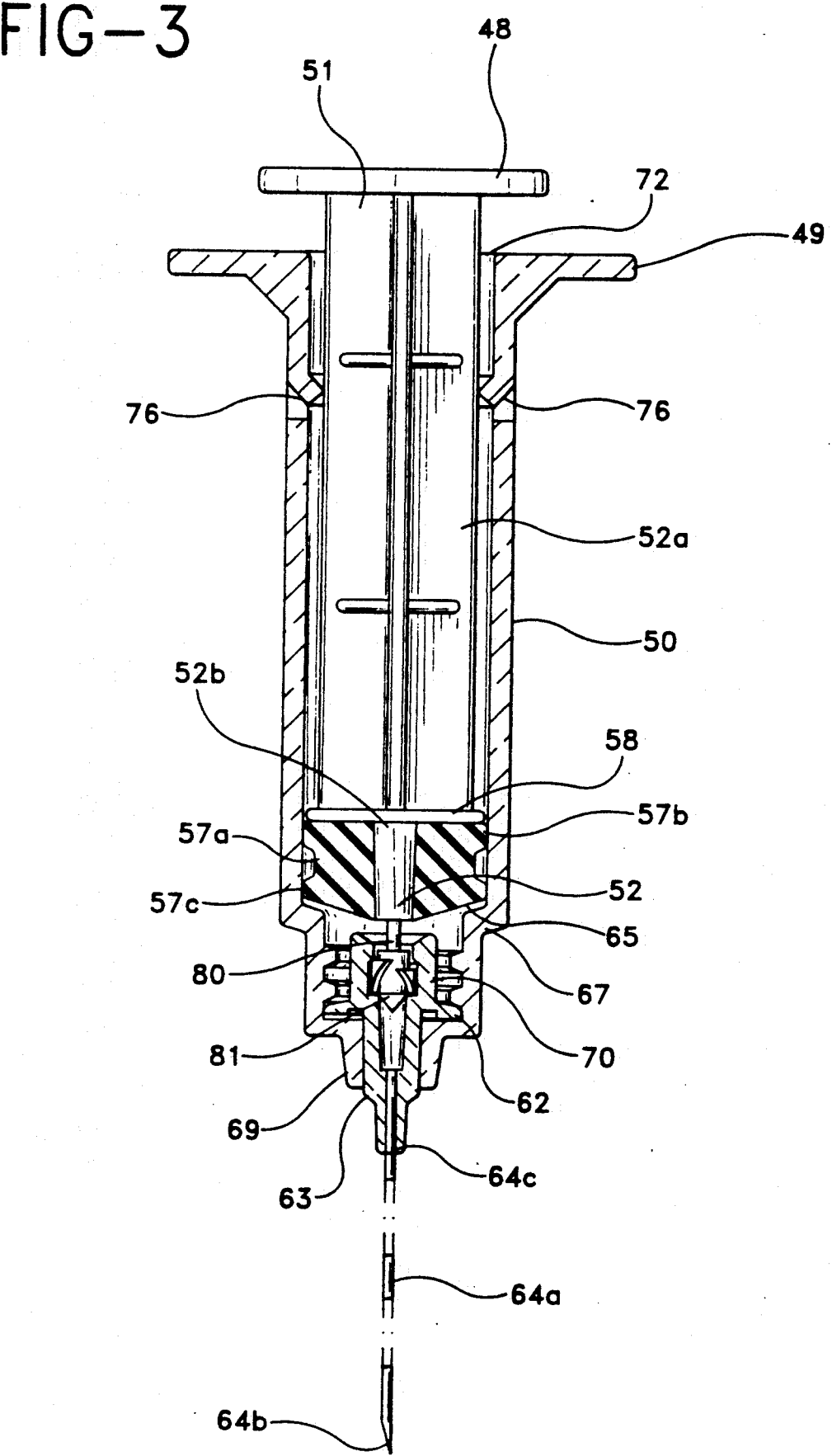
FIG. 3 is a partially sectioned side view of the embodiment shown in FIGS. 1-2 as it would appear with the plunger fully depressed within the syringe barrel.

Referring to FIG. 3, the positioning of the coupling assembly in the needle assembly is shown. As has been previously described, the proximal portion 80 of the coupling assembly supports the distal portion 81 of the coupling assembly at an angle relative to the longitudinal axis of the syringe barrel. When the plunger 51 is fully advanced into the syringe barrel, the distal portion 81 of the coupling assembly contacts the large tapered opening 75 of the needle assembly. The shape of the distal portion 81 and the tapered opening 75 guides the distal portion 81 into the needle assembly cavity 61 as the plunger 51 is advanced. The needle assembly cavity 61 is aligned with the longitudinal axis of the syringe barrel; thus the distal portion 81 is forced into alignment with the longitudinal axis. Since the distal portion 81 is guided into the cavity 61, the proximal portion 80 of the plunger head 52b, that supports the distal portion 81, is deformed from its standard position and orientation. The proximal portion 80 is constructed to elastically yield when deformed. Consequently, the proximal portion 80 acts as a cantilever spring between the distal portion and the base of the plunger head. The cantilever action of the proximal portion therefore applies a spring bias to the distal portion, when the proximal portion is deformed.

The distal portion 81 of the plunger head 52b includes in its construction an attachment means for engaging the needle base assembly and retracting the needle base assembly into the syringe barrel. The distal portion 81 of the plunger head 52b is a male connector that enters the cavity 61 in the needle base assembly, which is a female connector. In the technology of male and female connectors, many embodiments are well known in the art therein an operator can selectively connect a male and female connector by manipulating the male connector after it has entered a female connector. Any such technology can be used to couple the distal portion 81 of the plunger head 52b to the cavity 61 in the needle assembly. However, the embodiment shown utilizes the attachment means described in U.S. Pat. No. 4,986,813 which has been incorporated to this description by reference. As such, the present invention attachment means includes a plurality of triangular projections positioned on its exterior surface. The triangular projections are formed to rotatably engage with the interior of cavity 61 in a threadlike manner.

Utilizing the attachment means of U.S. Pat. No. 4,986,813 it can be seen that the distal portion 81 of the plunger head 52b can be locked into the cavity 61 of the needle base assembly by rotating the distal portion 81. The distal portion 81 is rotated by rotatably manipulating the gripping means 48 at the top of the plunger shaft. As the plunger 51 is rotated, the distal portion 81 of the plunger head 52b positively engages the needle assembly; however, the rotation of the plunger 51 may be continued causing the needle base assembly itself to rotate. The rotation of the needle base assembly causes the outwardly-directed projections 62 on the needle base assembly to unthread from the annular groove 66, formed on the syringe barrel neck. The rotation of the needle assembly is continued until the outwardly-directed projections 62 are clear of the annular groove 66. Once clear, the needle base assembly is free to be retracted into the syringe barrel.

As has been described, the positive engagement of the plunger head 52b and the needle assembly is created by the rotation of the plunger 51. If an operator desires to depress the plunger 51 fully into the syringe barrel without coupling the needle assembly, an operator does not rotate the plunger 51. Without the needed rotation, the syringe and needle assembly can be repeatedly used in the same manner as a typical hypodermic syringe.

Figure 4:
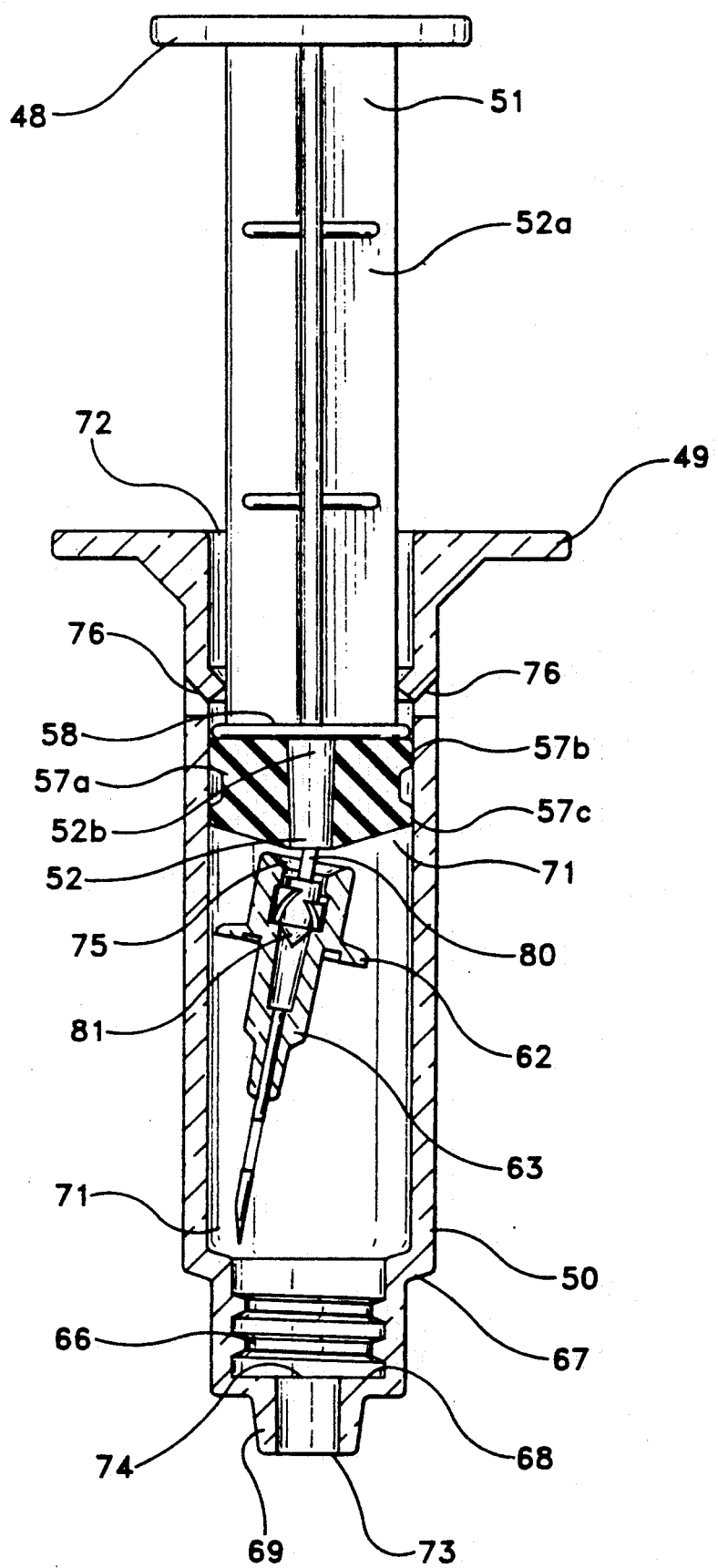
FIG. 4 is a partially sectioned side view of the embodiment shown in FIGS. 1-3 as it would appear with the needle assembly retracted into the syringe barrel.

Referring to FIG. 4, there is shown the needle assembly retracted into the syringe barrel. Once the outwardly-directed projections 62 on the needle assembly have been unthreaded from the neck of the syringe barrel, the plunger 51 can be retracted. The plunger 51 is now engaged with the needle assembly; consequently, the needle assembly is retracted into the syringe barrel as the plunger 51 is retracted. The positioning of the distal portion 81 of the plunger head 52b into the cavity 61 of the needle assembly, caused the proximal portion 80 of the plunger head 52b to elastically deform. As the needle assembly is retracted into the syringe barrel, there exists no forces to counteract the spring bias force of the elastically deformed proximal portion 80. Consequently, when the needle base assembly no longer contacts the neck of the syringe barrel, the proximal portion 80 of the plunger head 52b returns to its original undeformed position. The return of the proximal portion 80 of the plunger head 52b to its original position cants the position of both the plunger head distal portion 81 and the needle assembly. Once canted, the needle of the needle base assembly is no longer aligned with the longitudinal axis of the syringe barrel. Consequently, the sharp distal end 64b of the needle will engage the annular protrusion 67 on the neck of the syringe barrel, should the plunger 51 again be advanced.

Since the canting of the needle prevents the plunger from being advanced in the syringe barrel, the syringe and needle assembly is rendered inoperable and the danger presented by the needle is removed.

It will be understood that the embodiment described herein is merely exemplary and that a person skilled in the art may make variations and modifications without departing from the spirit and scope of the invention. As has been discussed, many known technologies can be used to join the piston head of the present invention to the needle base assembly. Additionally, many components of the exemplary embodiment have well known mechanical and functional equivalents that can be substituted for described components. For example, in the shown embodiment the spring bias, that cants the needle assembly, is created by the elastic deformation of the proximal portion 80 of the plunger, when the plunger is attached to the needle assembly. Many other spring biasing means can be used. In the incorporated by reference U.S. Pat. No. 4,986,813, a spring bias is created by a flexible protrusion that extends below the attachment means. The flexible protrusion is compressed and elastically deformed by the attachment of the piston to the needle assembly; thus, a spring bias is formed to cant the needle assembly. Such a spring bias means can be substituted for the spring bias means of the shown embodiments and are intended to be included within the scope of this invention as defined by the appended claims.

What is claimed is:

1. A hypodermic syringe and needle device comprising:
   a substantially cylindrical syringe barrel having an open proximal end and an open distal end;
   a retractable needle assembly, supporting a hollow needle, removably attached to said distal end of said syringe barrel, said needle assembly obstructing said distal end of said syringe barrel in a fluid impervious manner such that the flow of fluid through said distal end is directed through said hollow needle; and
   a plunger, extending through said open proximal end of said syringe barrel so as to be axially and reciprocally movable therein, said plunger having an attachment means thereon for selectively engaging said needle assembly and retracting said needle assembly into said syringe barrel, said plunger having a spring bias member, formed thereon biased into a set position, said spring bias member being deformed from said set position by the contact of said spring bias member against said needle assembly, when said attachment means on said plunger selectively engages said needle assembly, said spring bias member returning to said set position when said needle assembly is retracted into said syringe, thereby canting said needle assembly in said syringe barrel.

2. The device of claim 1, further including a stopping means for preventing said plunger from being withdrawn from said syringe barrel.

3. The device of claim 2, wherein said spring bias member joins said attachment means to said plunger.

4. The device of claim 3, wherein said needle assembly includes a receiving means for receiving said attachment means therein, said receiving means being formed to deform said spring bias member from said set position by the contact of said attachment means against said receiving means as said spring bias member passes into said receiving means, the deformation of said spring bias member from said set position said, creating a spring bias within said spring bias member.

5. The device of claim 4, wherein said attachment means attaches said piston to said needle assembly, when said attachment means is positioned within said receiving means and said attachment means is rotated relative to said receiving means.

6. The device of claim 5, wherein said spring bias member is a flexible cantilever member attaching to said piston, said cantilever member being formed said set position by the passage of said attachment means into said receiving means whereby said cantilever member returns to said set position when said needle assembly is retracted into said syringe barrel, canting said needle assembly within said syringe barrel.

7. The device of claim 5, wherein said needle assembly is threaded into said distal end of said syringe barrel, said needle assembly unthreading from said syringe barrel when engaged and rotated by said piston.

8. The device of claim 7, wherein said piston includes a gripping means to facilitate the rotation of said piston.

9. The device of claim 1, wherein said spring bias member is a flexible projection that depends from said plunger, said projection being elastically deformed against said needle assembly, as said attachment means attaches said plunger to said needle assembly, biasing said needle assembly into a canted position.

10. The device of claim 9, wherein said flexible projection extends from said attachment means towards said needle assembly so that said flexible projection is deformed by contacting said needle assembly as said plunger is attached to said needle assembly.

11. The device of claim 10, wherein said needle assembly includes a receiving means for receiving said attachment means therein, said attachment means attaching said piston to said needle assembly, when said attachment means is positioned within said receiving means and said attachment means is rotated relative to said receiving means.

12. The device of claim 11, wherein said needle assembly is threaded into said distal end of said syringe barrel, said needle assembly unthreading from said syringe barrel when engaged and rotated by said piston.

13. The device of claim 8, wherein said attachment means includes a plurality of substantial triangular projections, said projections joining with said receiving means in a threadlike manner when said attachment means is positioned within said receiving means and said attachment means is rotated relative to said receiving means.

14. The device of claim 9, wherein said attachment means and said flexible member are unstructurally formed from a plastic material.

15. The device of claim 8, wherein said attachment means includes a plurality of substantial triangular projections, said projections joining with said receiving means in a threadlike manner when said attachment means is positioned within said receiving means and said attachment means is rotated relative to said receiving means.

16. The device of claim 15, wherein said flexible projection causes said needle assembly to cant relative to said piston when said needle assembly is attached to said piston, and said needle assembly is retracted into said syringe barrel.

* * * * *